US009675463B2

(12) United States Patent
Lotke

(10) Patent No.: US 9,675,463 B2
(45) Date of Patent: Jun. 13, 2017

(54) PATELLO-FEMORAL PROSTHESIS

(76) Inventor: Paul A. Lotke, Gladwyne, PA (US)

( * ) Notice: Subject to any disclaimer, the term of this patent is extended or adjusted under 35 U.S.C. 154(b) by 556 days.

(21) Appl. No.: 12/480,350

(22) Filed: Jun. 8, 2009

(65) Prior Publication Data

US 2009/0248167 A1   Oct. 1, 2009

Related U.S. Application Data

(63) Continuation of application No. 10/773,684, filed on Feb. 4, 2004, now Pat. No. 7,544,209.

(60) Provisional application No. 60/535,967, filed on Jan. 12, 2004.

(51) Int. Cl.
*A61F 2/38* (2006.01)

(52) U.S. Cl.
CPC .. *A61F 2/3877* (2013.01); *A61F 2310/00029* (2013.01); *A61F 2310/00179* (2013.01)

(58) Field of Classification Search
USPC .......................... 623/20.18, 20.19, 20.2, 20.3
See application file for complete search history.

(56) References Cited

U.S. PATENT DOCUMENTS

| | | |
|---|---|---|
| 3,816,855 A | 6/1974 | Saleh |
| 3,852,830 A | 12/1974 | Marmor |
| 3,949,428 A | 4/1976 | Cavendish et al. |
| 3,953,899 A | 5/1976 | Charnley |
| 4,034,418 A | 7/1977 | Jackson et al. |
| 4,151,615 A | 5/1979 | Hall |
| 4,209,861 A | 7/1980 | Walker et al. |
| 4,216,549 A | 8/1980 | Hillberry et al. |
| 4,217,666 A | 8/1980 | Averill |
| 4,224,696 A | 9/1980 | Murray et al. |
| 4,309,778 A | 1/1982 | Buechel et al. |
| 4,340,978 A | 7/1982 | Buechel et al. |
| 4,457,307 A | 7/1984 | Stillwell |
| 4,462,120 A | 7/1984 | Rambert et al. |
| 4,470,158 A | 9/1984 | Pappas et al. |
| 4,568,348 A | 2/1986 | Johnson et al. |
| 4,574,794 A | 3/1986 | Cooke et al. |
| 4,586,933 A | 5/1986 | Shoji et al. |
| 4,770,663 A | 9/1988 | Hanslik et al. |

(Continued)

FOREIGN PATENT DOCUMENTS

| | | |
|---|---|---|
| DE | 2901009 | 7/1980 |
| DE | 3305237 | 8/1983 |

(Continued)

OTHER PUBLICATIONS

Cartier et al, Patellofemoral Arthroplasty, Journal of Arthroplasty, Mar. 1990, vol. 5, No. 1., p. 49-55.

(Continued)

*Primary Examiner* — Bruce E Snow
(74) *Attorney, Agent, or Firm* — Stephen H. Eland; Dann, Dorfman, Herrell & Skillman

(57) ABSTRACT

A patello-femoral prosthesis is provided for replacing the engagement surfaces between the patella and the femur. The prosthesis is configured to cover the trochlear groove and extend into the intercondylar notch without extending onto the articulating surfaces of the condyles. A method is also provided for implanting a patello-femoral prosthesis in which a portion of the trochlear groove and intercondylar notch are resected and the prosthesis is implanted over the femur that had portions resected.

17 Claims, 6 Drawing Sheets

(56) References Cited

U.S. PATENT DOCUMENTS

| | | |
|---|---|---|
| 4,822,366 A | 4/1989 | Bolesky |
| 4,950,298 A | 8/1990 | Gustilo et al. |
| 5,021,061 A | 6/1991 | Wevers et al. |
| 5,092,895 A | 3/1992 | Albrektsson et al. |
| 5,100,409 A | 3/1992 | Coates et al. |
| 5,116,375 A | 5/1992 | Hofmann |
| 5,123,927 A | 6/1992 | Duncan et al. |
| 5,147,406 A | 9/1992 | Houston et al. |
| 5,152,796 A | 10/1992 | Slamin |
| 5,181,925 A | 1/1993 | Houston et al. |
| 5,203,807 A | 4/1993 | Evans et al. |
| 5,219,362 A | 6/1993 | Tuke et al. |
| 5,226,916 A | 7/1993 | Goodfellow et al. |
| 5,282,866 A | 2/1994 | Cohen et al. |
| 5,326,359 A | 7/1994 | Oudard |
| 5,358,529 A | 10/1994 | Davidson |
| 5,358,531 A | 10/1994 | Goodfellow et al. |
| 5,370,699 A | 12/1994 | Hood et al. |
| 5,395,401 A | 3/1995 | Bahler |
| 5,405,395 A | 4/1995 | Coates |
| 5,405,398 A | 4/1995 | Buford, III et al. |
| 5,413,604 A | 5/1995 | Hodge |
| 5,549,684 A | 8/1996 | Amino et al. |
| 5,549,685 A | 8/1996 | Hayes |
| 5,549,688 A | 8/1996 | Ries et al. |
| 5,556,433 A | 9/1996 | Gabriel et al. |
| 5,569,259 A | 10/1996 | Ferrante et al. |
| 5,609,639 A | 3/1997 | Walker |
| 5,702,466 A | 12/1997 | Pappas et al. |
| 5,725,584 A | 3/1998 | Walker et al. |
| 5,728,162 A | 3/1998 | Eckhoff |
| 5,755,800 A | 5/1998 | O'Neil et al. |
| 5,755,803 A | 5/1998 | Haines et al. |
| 5,766,255 A | 6/1998 | Slamin et al. |
| 5,769,855 A | 6/1998 | Bertin et al. |
| 5,782,925 A | 7/1998 | Collazo et al. |
| 5,824,105 A | 10/1998 | Ries et al. |
| 5,871,541 A | 2/1999 | Gerber |
| 5,871,545 A | 2/1999 | Goodfellow et al. |
| 5,906,643 A | 5/1999 | Walker |
| 5,964,808 A | 10/1999 | Blaha et al. |
| 5,984,969 A | 11/1999 | Matthews et al. |
| 6,013,103 A | 1/2000 | Kaufman et al. |
| 6,123,729 A | 9/2000 | Insall et al. |
| 6,126,693 A | 10/2000 | O'Neil et al. |
| 6,139,580 A | 10/2000 | Wurzinger et al. |
| 6,165,223 A | 12/2000 | Metzger et al. |
| 6,168,629 B1 | 1/2001 | Timoteo |
| 6,171,340 B1 | 1/2001 | McDowell |
| 6,171,640 B1 | 1/2001 | Bringe |
| 6,190,415 B1 | 2/2001 | Cooke et al. |
| 6,197,064 B1 | 3/2001 | Haines et al. |
| 6,214,051 B1 | 4/2001 | Badorf et al. |
| 6,214,052 B1 | 4/2001 | Burkinshaw |
| 6,214,952 B1 | 4/2001 | Sadatoshi et al. |
| 6,231,611 B1 | 5/2001 | Mosseri |
| 6,235,060 B1 | 5/2001 | Kubein-Meesenburg et al. |
| 6,245,110 B1 | 6/2001 | Grundei et al. |
| 6,299,645 B1 | 10/2001 | Ogden |
| 6,364,911 B1 | 4/2002 | Schmotzer et al. |
| 6,383,222 B1 | 5/2002 | Badorf |
| 6,416,552 B1 | 7/2002 | Hoeppner et al. |
| 6,527,807 B1 | 3/2003 | O'Neil et al. |
| 6,554,866 B1 | 4/2003 | Aicher et al. |
| 6,582,469 B1 | 6/2003 | Tornier |
| 6,589,283 B1 | 7/2003 | Metzger et al. |
| 6,616,696 B1 | 9/2003 | Merchant |
| 6,712,856 B1 | 3/2004 | Carnignan et al. |
| 6,726,723 B2 | 4/2004 | Running |
| 6,743,258 B1 | 6/2004 | Keller |
| 6,893,467 B1 | 5/2005 | Bercovy |
| 2002/0138150 A1 | 9/2002 | Leclercq |
| 2002/0198528 A1 | 12/2002 | Engh et al. |
| 2003/0158606 A1 | 8/2003 | Coon et al. |
| 2003/0225457 A1 | 12/2003 | Justin et al. |
| 2003/0225458 A1* | 12/2003 | Donkers et al. ............ 623/20.15 |
| 2004/0167630 A1* | 8/2004 | Rolston ..................... 623/20.14 |
| 2006/0058884 A1 | 3/2006 | Aram et al. |

FOREIGN PATENT DOCUMENTS

| | | |
|---|---|---|
| EP | 0346183 | 12/1989 |
| EP | 0567705 | 11/1993 |
| EP | 0600806 | 6/1994 |
| EP | 0634155 | 1/1995 |
| EP | 0674887 | 10/1995 |
| EP | 0749734 | 12/1996 |
| FR | 2589720 | 11/1985 |
| FR | 2594323 | 4/1987 |
| FR | 2621243 | 10/1987 |
| FR | 2740325 | 4/1997 |
| FR | 2740326 | 4/1997 |
| FR | 2768329 | 3/1999 |
| FR | 2682287 | 10/2001 |
| GB | 2215610 | 9/1989 |
| GB | 2355935 | 5/2001 |
| JP | 58-203749 | 11/1983 |
| JP | 2002-524138 | 8/2002 |
| WO | 87/02882 | 5/1987 |
| WO | 95/14446 | 6/1995 |
| WO | 98/20818 | 5/1998 |
| WO | 99/13803 | 3/1999 |
| WO | 00/23010 | 4/2000 |
| WO | 00/23011 | 4/2000 |
| WO | 00/44316 | 8/2000 |
| WO | 03/070127 | 8/2003 |

OTHER PUBLICATIONS

Argenson et al, Is There a Place for Patellofermoral Arthoplasty, Clinical Orthopaedics and Related Research, 1995, 321, p. 162-167.

Arcieo et al, Patellofemoral Arthroplasty, Clinical Orthopaedics and Related Research, 1988, 236, p. 60-71.

Stockley et al, Bicondylar St. Georg Sledge Knee Arthroplasty, Clinical Orthopaedics and Related Research, 1990, 225, p. 228-234.

Product Specification for LCS PFJ Prothesis, published by DePuy Orthopaedics, Inc., 2000.

Product Specification for Patella Plannig System, published by DePuy Orthopaedics, Inc., 2000.

Product Brochure for LCS UNI-Unicompartmental Knee System, published by DePuy Orthopaedics, Inc., 1998.

Product Specification for Preservation-Uni-Compartmental Knee, published by DePuy Orthopaedics, Inc., 2002.

* cited by examiner

PATELLO-FEMORAL PROSTHESIS

PRIORITY CLAIM

This application is a continuation U.S. patent application Ser. No. 10/773,684, filed on Feb. 6, 2004, issued as U.S. Pat. No. 7,544,209 on Jun. 9, 2009. The entire disclosure of the foregoing application is hereby incorporated by reference.

This application claims priority to U.S. Provisional Patent Application No. 60/535,967, filed Jan. 12, 2004, which is hereby incorporated by reference.

FIELD OF THE INVENTION

The present invention relates to the field of prosthetics for knee replacement. More particularly, the present invention relates to a prosthesis for replacing the articulating surfaces of the knee. Specifically, the invention relates to a prosthesis for replacing the articulating surfaces of the patella and femur. In addition, the present invention relates to a method of repairing a knee, and specifically a method for repairing the articulating surfaces of the patella and femur.

BACKGROUND OF THE INVENTION

The knee is formed where the thigh bone meets the shin bone. The knee includes three bones, the femur (thigh bone), tibia (shin bone) and patella (knee cap). The distal end of the femur sits on top of the tibia, and the patella is on the front of the femur.

The three bones in the knee form two joints. The first is the tibio-femoral joint, which relates to the joint where the femur meets tibia. The second joint is the patello-femoral joint, which relates to the joint where the patella meets the femur.

The joint elements that engage one another are covered by articular cartilage. Specifically, the distal end of the femur and the proximal end of the tibia are covered by articular cartilage, as is the posterior surface of the patella. The articular cartilage is a slippery substance that absorbs shock and allows the bone surfaces to slide against one another without damage to either surface.

If the articular cartilage becomes damaged, the contact surface in the joint will not slide as well. The damaged area becomes a weak point in the cartilage that is prone to continued degradation over time. Ultimately, the damage can lead to bone-to-bone contact during articulation of the joint, resulting in significant pain and potential damage to the bone surfaces.

If the damage to the articular cartilage is sufficient enough, a knee replacement procedure may be required. Depending on the extent of the damage, the procedure may operate on either all or only a portion of the knee. For instance, in a total knee replacement, the ends of both the femur and the tibia are covered by prosthetics, as well as a surface of the patella. In other instances the procedure may be limited to portions of one of the joints. For instance, in a patello-femoral procedure, the procedure is limited to the engagement surfaces between the femur and the patella.

SUMMARY OF THE PREFERRED EMBODIMENTS

A patello femoral prosthesis is provided for repairing surfaces of the patello-femoral joint. A patella prosthesis is provided for replacing a surface of the patella and a femoral prosthesis is provided for replacing surfaces of the femur. The patella prosthesis is configured to cooperate with a groove in the femoral prosthesis. The femoral prosthesis is configured to overlay a portion of the trochlear groove and the intercondylar notch of the femur. Preferably, the femoral prosthesis is configured to cooperate with a unicompartmental prosthesis that is configured to cover an articular surface of one of the condyles of the femur.

A method for implanting a patello-femoral prosthesis is also provided. A portion of the patella is resected and a patellar prosthesis is attached to the patella. A portion of the trochlear groove and a portion of the intercondylar notch are also resected to form a recess. Preferably, the resected portion of the intercondylar notch extends along the medial and lateral condyles, and terminates without extending onto an articular surface of one of the condyles. A femoral prosthesis is inserted into the recess formed by resecting the femur, and the prosthesis is attached by either a cementing or non-cementing process.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

Figure 1:
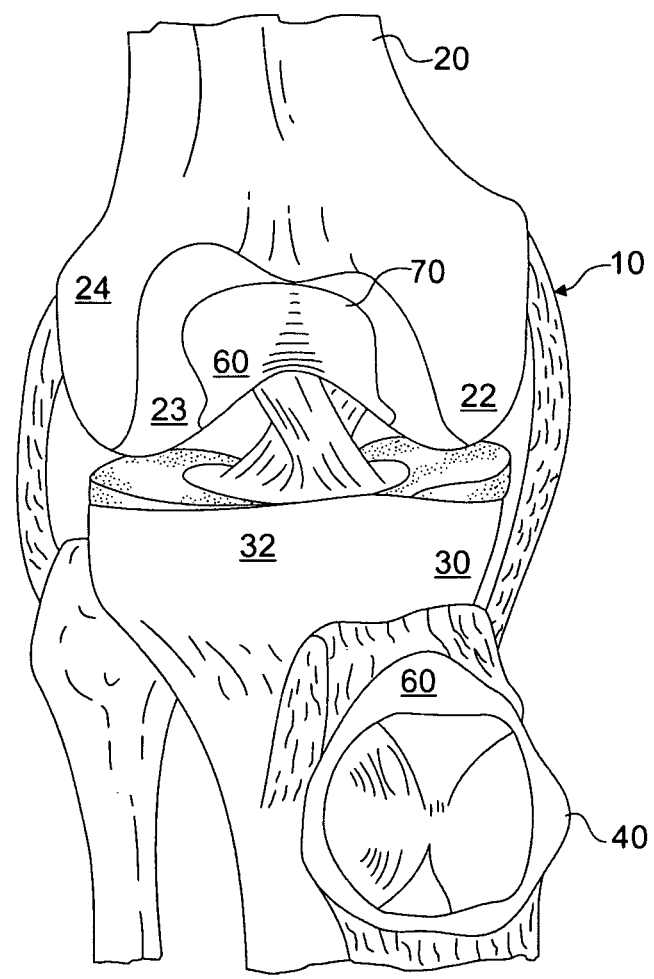
FIG. 1 is an anterior view of a knee with a patello-femoral prosthesis.

Referring now to the figures, wherein like elements are numbered alike throughout, a patello-femoral prosthesis 50 is illustrated. In one aspect, the prosthesis includes a patellar prosthesis 60 and a femoral prosthesis 70 that operate as replacement surfaces for the interaction between the patella and the femur. Specifically, the patellar prosthesis 60 covers a surface of the patella and the femoral prosthesis 70 covers a surface of the femur that cooperates with the patella during flexion and extension of the leg.

The features of the patello-femoral prosthesis 50 are configured to cooperate with various features of the femur 20 and the patella 40. Accordingly, the following description details the features of the femur and the patella related to the features of the prosthesis, which are described more fully below.

The patella 40 is a small bone embedded within the patella tendon in front of the intersection of the femur and the tibia (to shown the details of the knee in FIG. 1, the patella is shown with the patella tendon detached from the femur and folded over). The patella 40 normally lies at the top of the groove, or trochlear 25, of the femur 20. As the knee bends, it slides along the trochlear groove 25, held in place by various ligaments and other tissues. As the knee bends past about 30 degrees, the patella 40 moves slightly towards the center of the body, centering it in this groove. As the knee bends even farther, the patella continues to slide along the trochlear groove.

As mentioned previously, the knee 10 includes two joints: the joint between the femur and the tibia (referred to as the tibio-femoral joint), and the joint between the femur and the patella (referred to as the patello-femoral joint).

The tibio-femoral joint is characterized by interaction between condyles 22, 24 at the distal end of the femur 20 and the tibial plateau 32 at the proximal end of the tibia 30. Specifically, the distal end of the femur includes a pair of condyles: the medial condyle 22 and the lateral condyle 24. The condyles are generally ovoid in shape and have articular surfaces 23 covered by articular cartilage that cooperates with the tibia. Specifically, the condyles cooperate with the tibial plateau 32, which also has portions covered by articular cartilage. The articular surfaces are smooth surfaces configured to provide bearing surfaces for the rotation of the tibia relative to the femur during flexion of the knee.

Figure 2:
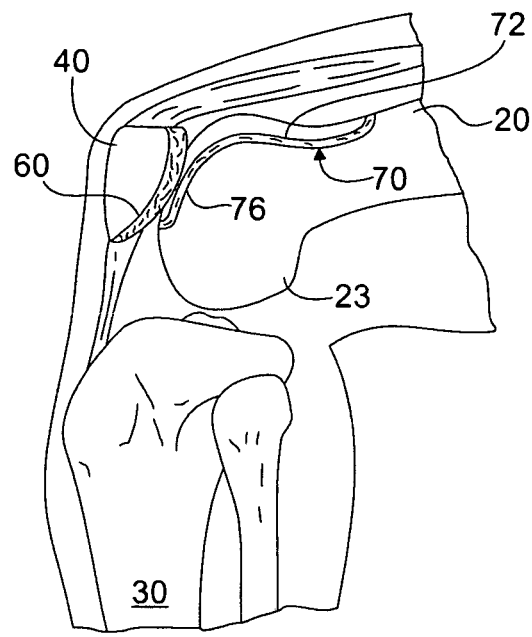
FIG. 2 is a lateral view partially in section of the knee and prosthesis in FIG. 1.
Figure 6:
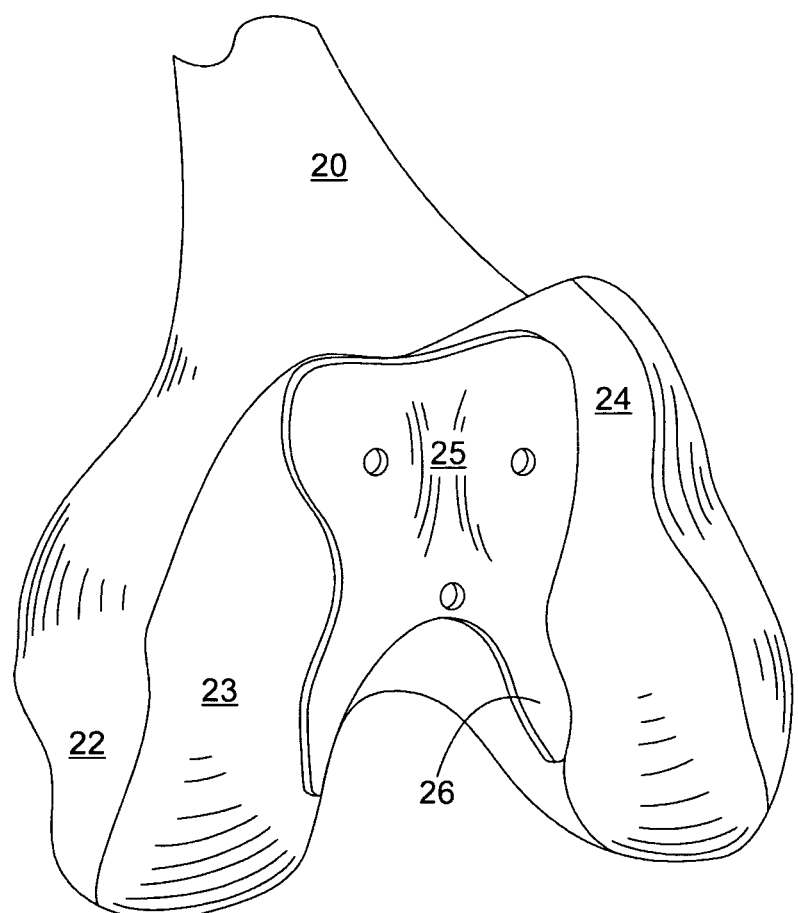
FIG. 6 is a distal perspective view of a distal end of a partially resected femur.
Figure 7:
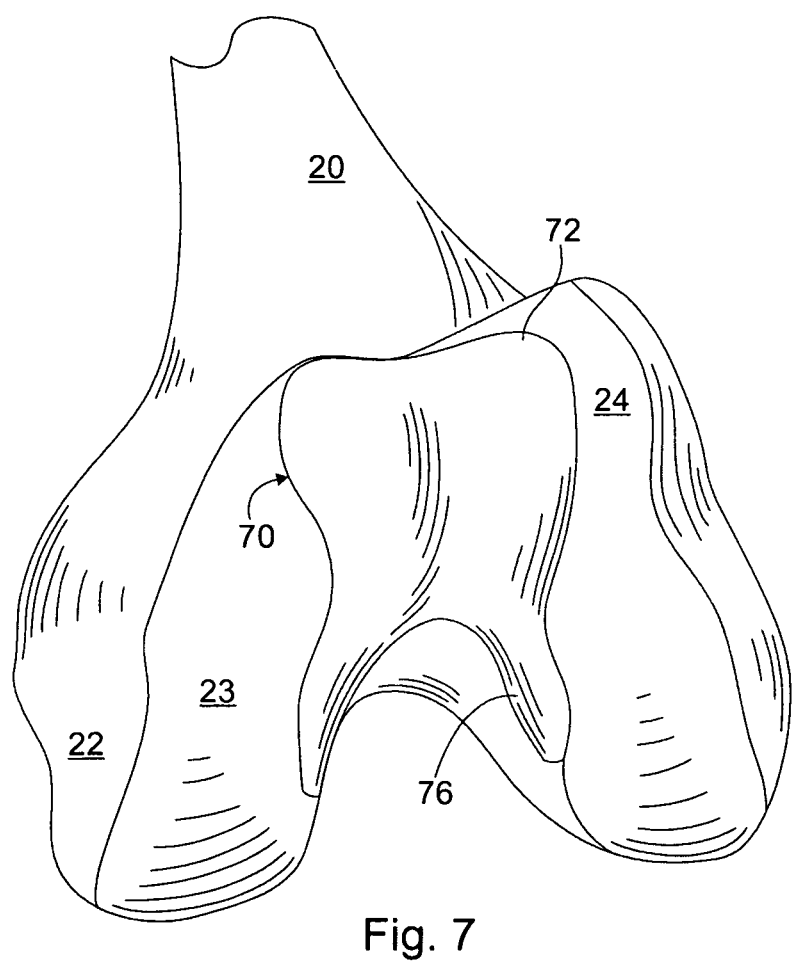
FIG. 7 is a distal perspective view of the femur illustrated in FIG. 6, illustrated with the femoral component illustrated in FIG. 3 implanted.

The articular surfaces 23 of the condyles generally extend from the distal end of the femur around to the posterior side of the femur, as shown in FIGS. 2, 6 The articular surfaces of the medial and lateral condyles 22, 24 are separated from one another. An intercondylar notch 26 extends between the two condyles.

The trochlear groove 25 extends along the anterior surface of the femur 20, extending toward the distal end of the femur. The trochlear groove is a groove that the patella 40 slides within, as discussed further below. The trochlear groove includes a central groove, having sidewalls that curve upwardly, so that the sidewalls from convex surfaces. More specifically, the groove 25 is a concave groove that extends toward the distal end of the femur, while the sidewalls extend upwardly and away from the groove, so that the trochlear groove is saddle-shaped. The distal end of the trochlear groove 25 intersects the intercondylar notch 26.

The patella is a small bone situated within the tendon of the quadriceps muscle just above the point where the tendon joins onto the tibia. The patellar bone provides a significant mechanical advantage to the knee extensor mechanism, allowing the knee to extend with a smaller contractile force of the quadriceps. In addition, the patella redirects the force exerted by the quadriceps, resulting in a large compressive stress on the patello-femoral joint. The magnitude of this stress usually is at a maximum with the knee flexed between about 45-60° and the foot planted, such as that occurring when one stands from a sitting position.

The posterior surface of the patella 40 forms a surface that is configured to slide within the trochlear groove 25 during flexion of the knee. Specifically, as shown in FIG. 1 the posterior surface of the patella forms a generally V-shaped surface that cooperates with the trochlear groove. The confronting surfaces of the patella and the trochlear groove are covered in articular cartilage so that the two bones readily slide relative to one another during knee flexion.

Only a portion of the patellar cartilage articulates with the femoral trochlea at any one time. With the knee extended 0°, the patella rides laterally within the trochlear groove and is not in direct contact with the trochlear cartilage. With knee flexion, the patella moves distally, and the degree of surface contact of the patello-femoral joint increases. For instance, the initial contact of the patella with the femur occurs at approximately 20°. By 90° of flexion a substantial portion of the articular surface of the patella has made contact with the femur. Beyond 90° of flexion, the patella rides down into the intercondylar notch and the quadriceps ride in the trochlear groove.

The muscles and tendons of the quadriceps don't form a straight line when viewed from the front. They point one way above the patella and another way below the patella. Therefore when the muscles contract, the kneecap has a tendency to be pulled off to the side. The sidewalls of the trochlear groove retain the patella within the trochlear groove. The contours of the posterior surface of the patella and the trochlear groove determine the stability of the patello-femoral joint. For instance, if the trochlear groove is shallow, the patella is more easily pulled laterally out of the trochlear groove during flexion of the knee (referred to as patellar subluxation).

Since the two joints in the knee have different articular surfaces and since the two joints are subject to different forces, one of the joints may require replacement, but the other may be sufficiently healthy that it does not need replacement. Therefore, it is often desirable to replace select articular surfaces without replacing all of the articular surfaces in the knee.

If there is damage to the patello-femoral joint, it is desirable to replace the articulating surfaces of the patella 40 and the femur 20. Further, if the tibio-femoral joint does not need repair, it is desirable to replace to patello-femoral surfaces without affecting the tibio-femoral surfaces. This can be accomplished by implanting a patellar prosthesis 60 and a femoral prosthesis 70. Preferably, the femoral prosthesis replaces the surfaces of the trochlear groove 25 and extends into the intercondylar notch 26, without overlapping the articular surfaces of the tibio-femoral joint. The patellar prosthesis 60 replaces a posterior surface of the patella and is configured to slidingly engage the femoral prosthesis 70.

The patellar prosthesis 60 is preferably a single element that is configured to re-surface a portion of the posterior surface of the patella. As described previously, the posterior surface of the patella forms a generally V-shaped surface configured to ride in the trochlear groove. Similarly, preferably the posterior surface of the patellar implant forms a projection that is configured to cooperate with a groove in the femoral implant as discussed below. Preferably, but not necessarily, the interfacing prostheses are formed of different materials. Accordingly, the patellar prosthesis 60 and the femoral prosthesis 70 are preferably formed of different materials, such as plastic and metal. In the preferred embodiment, the patellar prosthesis is formed of a plastic, such as ultra-high molecular weight (UHMW) polyethylene, and the femoral prosthesis is formed of metal, such as cobalt-chromium molybdenum. However, other materials may be utilized, such as ceramics or other plastic or metals.

Figure 3:
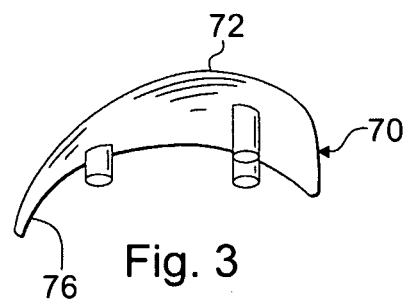
FIG. 3 is a perspective view of a femoral component of the prosthesis in FIG. 1.
Figure 4:
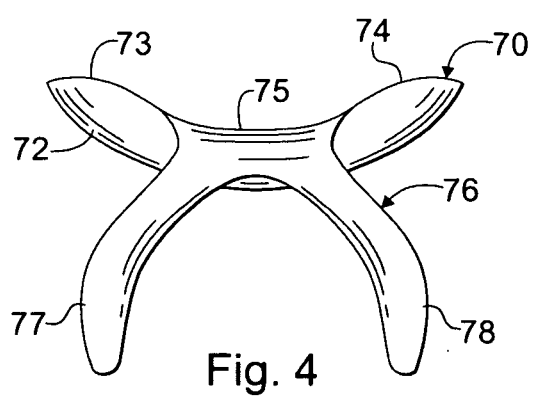
FIG. 4 is a distal view of the femoral component shown in FIG. 3.
Figure 5:
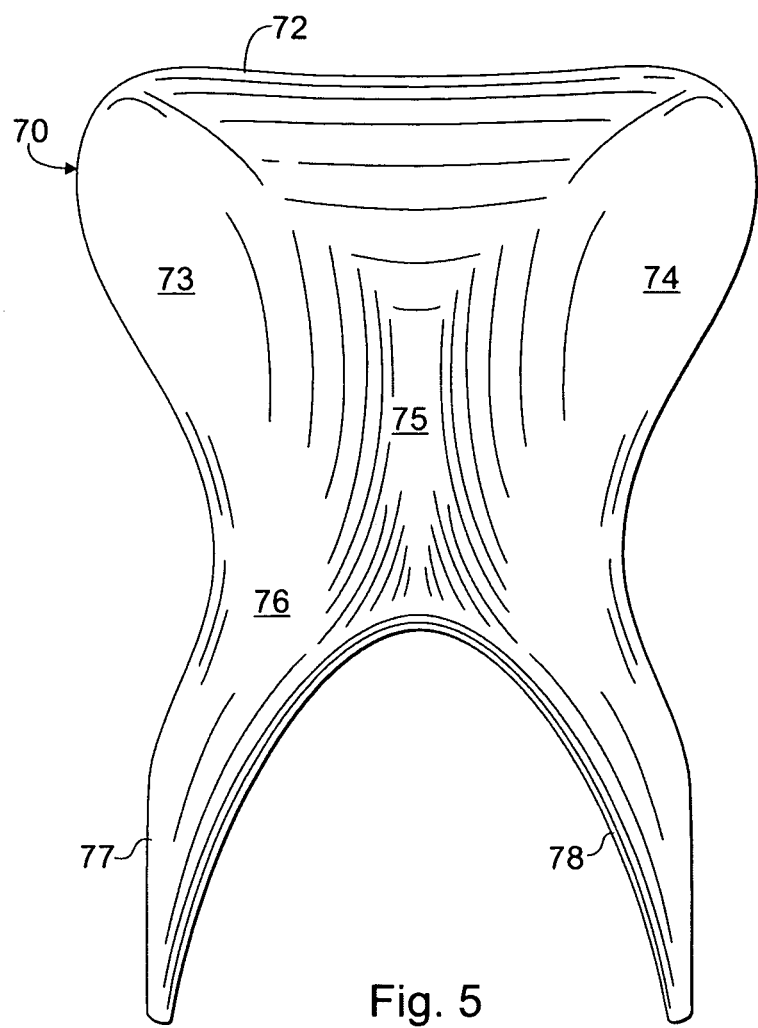
FIG. 5 is a distal perspective view of the femoral component shown in FIG. 3.

Referring now to FIGS. 3-5, the details of the femoral prosthesis 70 will now be described in greater detail. The femoral prosthesis includes two sections. Preferably the two sections form a single unitary element. However, the femoral prosthesis may be formed of a plurality of separate elements.

The first section of the femoral prosthesis is the central or trochlear portion 72 that is configured to cover the trochlear groove. The second section is the intercondylar section 76 that intersects the distal end of the trochlear portion. The intercondylar portion 76 preferably comprises a pair of tapered extensions 77,78 configured to extend into away from the trochlear portion along the intercondylar notch adjacent the interior edges of the condyles.

In general, the trochlear portion 72 provides a channel for retaining the patella 40 in place (i.e. preventing subluxation) and providing a sliding surface in which the patella can slide during moderate bending of the knee. The intercondylar portion 76 provides a sliding portion on which the patella can slide during deep bending of the knee.

The trochlear portion 72 is an elongated element that flares outwardly adjacent its proximal end, and narrows adjacent the distal end adjacent the intercondylar portion 76. A groove 75 extends along the top surface of the trochlear portion, extending from the proximal end to the distal end. In certain configuration, it may be desirable to center the groove between the sides of the trochlear portion. Sidewalls 73, 74 extend upwardly and away from the groove. The sidewalls 73, 74 are configured to retain the patella 40 within the groove 75. In a preferred embodiment, the sidewalls curve upwardly forming a convex surface. In this way, the groove 75 is concave, having upwardly extending convex sidewalls. Although the sidewalls have been described as convex curved surfaces, the sidewalls need not be curved. The sidewalls can be configured to extend upwardly generally straight to form a channel, such as a V-groove. However, even such sidewalls would preferably be convex, because preferably, the upper edge of the sidewalls curves or bends over to overlie the femur (See e.g. FIG. 4).

As described above, the trochlear portion 72 has a groove that is generally convex in the direction of the width of the femur. In addition, preferably the trochlear portion curves downwardly toward the posterior as the trochlear portion extends toward the intercondylar notch. In this way, the trochlear portion is generally convex in the direction of the length of the femur.

The intercondylar portion 76 intersects the distal end of the trochlear portion and extends downwardly in a posterior direction and away from the trochlear portion. The intercondylar portion has a pair of opposing extensions configured to extend along the sides of the intercondylar notch. The first extension projects is a medial extension 77 that extends in a medial direction and downwardly in a posterior direction. The medial extension is configured to overlie a medial portion of the intercondylar notch 26 without extending onto an articular surface 23 of the medial condyle 22. The second extension is a lateral extension 78 that is configured similarly to the medial extension 77, except that it extends in a lateral and posterior direction, away from the medial extension. Further, the lateral extension 78 is configured to overlie a lateral portion of the intercondylar notch 26 without extending onto an articular surface of the lateral condyle 24.

Referring to FIG. 4, the medial and lateral extensions 77, 78 form a generally arch-shaped extension that curves outwardly and posteriorly. Preferably, the extensions taper as they extend away from trochlear portion 72. In this way, the ends of the extensions remote from the trochlear portion are narrower than the width of the extension adjacent the trochlear portion. The two extensions are configured to provide a surface upon which the patella slides when the knee is bent during deep flexion. Specifically, each extension operates as a rail upon which the posterior surface of the patella rides—the lateral side of the posterior patella surface rides on the lateral extension, the medial side rides on the medial extension.

As described above, the trochlear 72 and intercondylar portions 76 of the femur prosthesis have been described as being symmetric. However, the femoral prosthesis 70 need not be symmetric. Since the femur and tibia do not form a straight line, when the knee is bent, the patella is pulled distally and inwardly (in a medial direction). Therefore, typically, the medial side of the condyle is larger and the medial side of the trochlear groove is higher than the lateral side to retain the patella within the intercondylar groove. The femoral prosthesis 70 may be configured to reflect this lack of symmetry. For instance, the medial sidewall 73 of the trochlear portion 72 may be higher than the lateral sidewall 74. Similarly, the medial extension 77 may be wider and/or longer than the lateral extension 78 of the intercondylar portion.

The foregoing discussion has described features of the femoral prosthesis for replacing the articular surfaces of the patello-femoral joint. In some instances, it may be desirable to replace some of the surfaces of the tibio-femoral joint in addition to the patello-femoral joint. For instance, the interface between the medial condyle and the tibial plateau may be damaged and need replacement. Accordingly, it may be desirable to repair the interface while repairing the patello-femoral joint. Furthermore, if the interface between the lateral condyle and the tibial plateau are not sufficiently damaged to justify replacement, it is desirable to repair the patello-femoral joint and the medial condyle/tibial plateau surfaces without altering the surfaces of the lateral condyle/tibial plateau interface.

Figure 8:
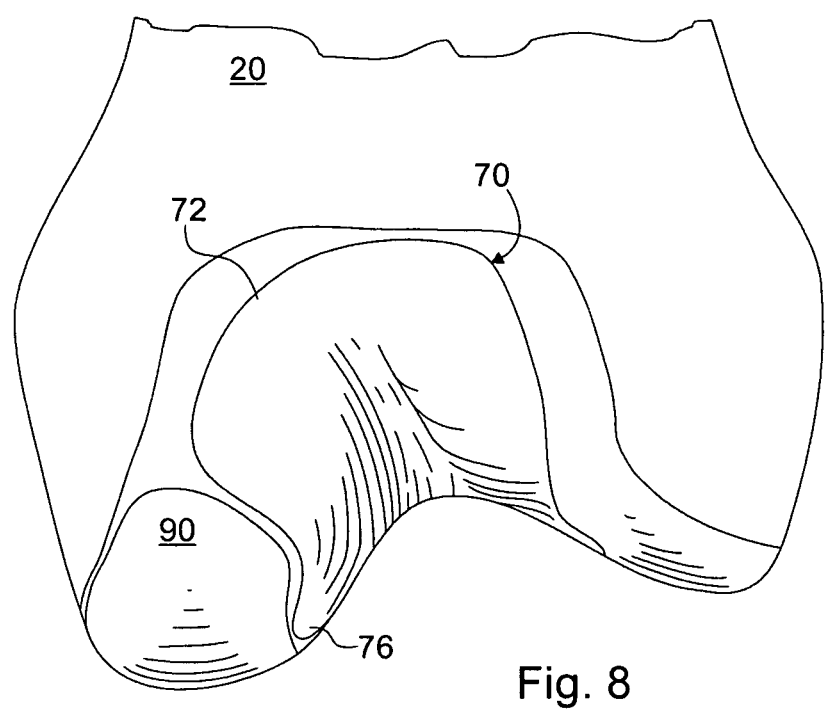
FIG. 8 is a distal perspective view of a femur with the femoral component illustrated in FIG. 3 combined with a unicompartmental prosthesis.

To facilitate selective repair of the knee joint surfaces, a unicompartmental femoral prosthesis 90 is utilized to replace the articular surface of the medial condyle. (see FIG. 8) Specifically, the unicompartmental prosthesis 90 is configured to cover the articular surface of the medial condyle. Preferably, the prosthesis has a generally C-shaped configuration adapted to overly the outer surface of the medial condyle. Further, preferably the unicompartmental prosthesis is wide enough to cover the articular surface, but it has a lateral side edge that terminate adjacent to the lateral edge of the articular surface. In addition, preferably the femoral prosthesis described above is configured to cooperate with the unicompartmental prosthesis so that the edges of the two prostheses cover the condylar and intercondylar articular surfaces without overlapping each other.

Method of Implanting

The patello-femoral prostheses are preferably implanted as follows. Since the patella is embedded within the patellar tendon it is generally desirable to repair the patella rather than replacing the patella. To implant the patellar prosthesis 60, a portion of the patella is resected, and the patella prosthesis is attached to the patella. Specifically, a portion of the posterior prosthesis, preferably less than 10 mm thick, is resected from the patella. The patella prosthesis is then attached using an adhesive. In addition, the prosthesis may include a tab or post to improve the bonding between the prosthesis and the patella. Therefore, in addition to cutting-off a portion of the posterior patellar surface, a recess may be drilled into the patella to receive the post on the prosthesis. Adhesive cement is then applied to the posterior surface of the patella and the prosthesis is pressed into the cement to bond the prosthesis to the patella. In this way, the patellar articulating surface is replaced by the prosthesis.

To replace the femoral surfaces, the surfaces of the trochlear groove and the intercondylar notch are resected and the femoral prosthesis is bonded onto the femoral surfaces from which bone was resected. Specifically, the surface of the trochlear groove is resected to form a recess of preferably no greater than 10 mm. In addition, preferably the recess extends to the anterior surface of the femur adjacent the trochlear groove. The shape of the recess is configured to be substantially similar to the outline of the trochlear portion of the femoral prosthesis, and preferably the recess is deeper than the thickness of the trochlear portion.

In addition, the femur is further resected along the intercondylar notch to accommodate the intercondylar notch portion of the femoral prosthesis. The intercondylar notch is resected to form a recess extending along the intercondylar groove. The recess extends along the medial condyle terminating adjacent the articular surface of the medial condyle so that the recess does not extend onto the articular surface of the medial condyle. Similarly, the recess extends along the intercondylar notch onto the lateral condyle, terminating adjacent the articular surface of the lateral condyle so that the recess does not extend onto the articular surface of the lateral condyle. Preferably, the recess on the intercondylar notch intersects the recess on the trochlear groove to form one continuous recess.

After portions of the distal end of the femur are resected as described above, preferably the femoral prosthesis is bonded into the recess using adhesive cement. Specifically, adhesive cement is applied to the recess and the femoral prosthesis is then pressed into the cement to bond the prosthesis to the femur. The femoral prosthesis may be a single unitary element so that the entire prosthesis in implanted at once. Alternatively, the prosthesis may be comprised of several separate elements that are implanted separately. More specifically, after the cement is applied to the recess each piece of the prosthesis is pressed into the cement. By using a multi-element prosthesis, the size of the incision necessary to insert the prosthesis can be reduced.

As discussed previously, in certain instances it may be desirable to repair surfaces of the tibio-femoral joint during the same procedure for repairing the patella-femoral joint. For instance, to implant a unicompartmental prosthesis over one of the condyles, the recess in the distal end of the femur is extended onto the surface of one of the condyles. For instance, to repair the lateral condyle, the recess along the lateral portion of the intercondylar groove is extended onto the articular surface of the lateral condyle. Adhesive cement is then applied to the recess and the unicompartmental prosthesis is pressed into the cement so that the unicompartmental prosthesis overlies the surface of the lateral condyle. A unicompartmental prosthesis can be implanted over the medial condyle in a similar fashion (i.e. extending the recess onto the medial condyle and bonding the prosthesis over the medial condyle). When inserting the femoral prosthesis with a unicompartmental prosthesis, preferably the prostheses are positioned so that the adjoining edges of the prostheses are adjacent without overlapping.

In the above description, the prostheses are described as being implanted by cementing the prostheses. However, the prostheses may be implanted using any one of a variety of bonding procedures. For instance, any of a variety of procedures using adhesives or chemical can be used. Also, porous growth techniques can be used in which the surface of the prosthesis has a fine mesh of holes that allows bone to grow into the mesh to attach the prosthesis to the bone. Accordingly, there is no intention to limit the method of implanting to any particular bonding process.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. A knee prosthesis for covering a portion of a patient's patella, and trochlear groove and intercondylar notch of the femur, comprising:
   a patellar prosthesis configured to cover a posterior surface of a patella; and
   a femoral prosthesis comprising:
      a body having a posterior surface configured to cover a portion of the trochlear groove and an anterior surface forming a groove that is cooperable with the posterior surface of the patellar prosthesis;
   and at least one of either:
      a medial extension having a posterior surface configured to engage a portion of the intercondylar notch of the patient, wherein the medial extension projects away from a distal end of the body and is configured to extend along a medial edge of the intercondylar notch to engage a substantial length of the medial side of the intercondylar notch; and
      a lateral extension having a posterior surface configured to cover a portion of the intercondylar notch, wherein the lateral extension projects away from a distal end of the body and is configured to extend along a lateral edge of the intercondylar notch to engage a substantial length of the lateral side of the intercondylar notch;
   wherein the femoral prosthesis is configured to form an articular surface between the patella and the femur without substantially overlying an articular surface between the femur and the tibia; and
   wherein the at least one extension has a length and a width at an intersection with the body, wherein the length is substantially greater than the width.

2. The prosthesis of claim 1 wherein the femoral prosthesis comprises both medial and lateral extensions and the medial and lateral extensions intersect the body to form a generally U-shaped configuration.

3. The prosthesis of claim 1 wherein the femoral prosthesis comprises both medial and lateral extensions and the medial and lateral extensions form opposing sides of a bearing surface configured to cooperate with the patellar prosthesis.

4. The prosthesis of claim 1 wherein the femoral prosthesis comprises the medial extension and the medial extension has a length and a width and the length is substantially greater than the width.

5. The prosthesis of claim 4 wherein the femoral prosthesis comprises the lateral extension and the lateral extension has a length and a width and the length is substantially greater than the width.

6. The prosthesis of claim 1 wherein the femoral prosthesis comprises both medial and lateral extensions and the medial extension has an inner edge opposing the lateral extension and an outer edge, wherein the outer edge is configured to terminate over the intercondylar notch without extending over an articular surface of the medial condyle.

7. The prosthesis of claim 1 wherein the femoral prosthesis comprises both medial and lateral extensions and the medial extension has an inner edge opposing the lateral extension and an outer edge, wherein the outer edge of the medial extension comprises a generally convexly-shaped curve.

8. The prosthesis of claim 1 wherein the femoral prosthesis comprises both medial and lateral extensions and the lateral extension has an inner edge opposing the medial extension and an outer edge, wherein the outer edge is configured to terminate over the intercondylar notch without extending over an articular surface of the lateral condyle.

9. The prosthesis of claim 1 wherein the femoral prosthesis comprises both medial and lateral extensions and the lateral extension has an inner edge opposing the medial extension and an outer edge, wherein the outer edge of the lateral extension comprises a generally convexly-shaped curve.

10. A femoral prosthesis, comprising:
a trochlear groove portion having an anterior surface forming a groove that is configured to cooperate with a posterior surface of a patellar prosthesis; and
an intercondylar notch portion connected with the troclear groove projecting transverse the trochlear groove portion, wherein the intercondylar notch portion is configured to form a patellar-femoral articular surface without substantially overlying a condylar surface of a femoral-tibial articular surface, wherein a rearward surface of the intercondylar notch portion is configured to engage the bone of a patient and the rearward surface curves laterally and posteriorly to overlie the intercondylar notch, and wherein the intercondylar notch portion has an exterior edge that curves laterally or medially away from the trochlear groove portion.

11. The femoral prosthesis of claim 10 wherein the intercondylar notch portion has an interior edge and an exterior edge, wherein both the interior edge and the exterior edge curve away from the trochlear groove portion along substantially the entire length of the intercondylar notch portion.

12. The prosthesis of claim 10 wherein the intercondylar notch portion tapers so that a distal end of the intercondylar notch portion remote from the trochlear groove portion is narrower than the width of the intercondylar notch portion adjacent the trochlear groove portion.

13. A femoral prosthesis, comprising:
a body having a posterior surface configured to engage a portion of a patient's femur and an anterior surface forming a groove that is configured to cooperate with a posterior surface of a patellar prosthesis; and
an intercondylar notch portion connected with the body having a posterior surface configured to engage a second portion of the patient's femur, wherein the intercondylar notch portion has outer edges that terminate so that the intercondylar notch portion is configured to overlie a portion of the intercondylar notch without substantially extending over an articular surface between a condyle and the tibia, wherein the intercondylar notch portion comprises a medial extension having a medial edge and a lateral extension having a lateral edge, wherein the medial edge diverges from the lateral edge so that the medial and lateral extensions diverge.

14. The prosthesis of claim 13 wherein the medial and lateral extensions form opposing sides of a bearing surface configured to cooperate with a patellar prosthesis.

15. The prosthesis of claim 13 wherein the medial and lateral extensions project away from the body forming a gap between the medial and lateral extension.

16. The prosthesis of claim 13 wherein the body tapers inwardly from medial and lateral directions to form a narrow waist adjacent the intercondylar notch portion.

17. The prosthesis of claim 13 wherein the medial and lateral extensions comprise anterior and posterior curved surfaces and the posterior surface curves to follow the curvature of the anterior surface.

\* \* \* \* \*